United States Patent
Nofrey et al.

(10) Patent No.: US 8,801,782 B2
(45) Date of Patent: Aug. 12, 2014

(54) SURGICAL METHODS FOR BREAST RECONSTRUCTION OR AUGMENTATION

(75) Inventors: Barbara Nofrey, Goleta, CA (US); Dennis Van Epps, Goleta, CA (US)

(73) Assignee: Allergan, Inc., Irvine, CA (US)

( * ) Notice: Subject to any disclaimer, the term of this patent is extended or adjusted under 35 U.S.C. 154(b) by 0 days.

(21) Appl. No.: 13/327,473

(22) Filed: Dec. 15, 2011

(65) Prior Publication Data
US 2013/0158657 A1 Jun. 20, 2013

(51) Int. Cl.
*A61F 2/12* (2006.01)

(52) U.S. Cl.
USPC ............................................... 623/8; 128/898

(58) Field of Classification Search
USPC .......................................................... 623/7, 8
See application file for complete search history.

(56) References Cited

U.S. PATENT DOCUMENTS

| | | |
|---|---|---|
| 2,324,735 A | 1/1941 | Spanel |
| 2,805,208 A | 9/1957 | Roche |
| 3,189,921 A | 6/1965 | Pangman |
| 3,293,663 A | 12/1966 | Cronin |
| 3,366,975 A | 2/1968 | Pangman |
| 3,559,214 A | 2/1971 | Pangman |
| 3,600,718 A | 8/1971 | Boone |
| 3,665,520 A | 5/1972 | Perras |
| 3,700,380 A | 10/1972 | Kitrilakis |
| 3,852,832 A | 12/1974 | McGhan |
| 3,934,274 A | 1/1976 | Hartley |
| 4,034,751 A | 7/1977 | Hung |
| 4,157,085 A | 6/1979 | Austad |
| 4,231,979 A | 11/1980 | White |
| 4,237,237 A | 12/1980 | Jarre et al. |
| 4,264,990 A | 5/1981 | Hamas |
| 4,298,997 A | 11/1981 | Rybka |
| 4,298,998 A | 11/1981 | Naficy |
| 4,329,385 A | 5/1982 | Banks |
| 4,428,082 A | 1/1984 | Naficy |
| 4,433,440 A | 2/1984 | Cohen |
| 4,470,160 A | 9/1984 | Cavon |
| 4,482,577 A | 11/1984 | Goldstein |
| 4,499,211 A | 2/1985 | Walch |
| 4,531,244 A | 7/1985 | Hamas |
| 4,573,999 A | 3/1986 | Netto |
| 4,584,324 A | 4/1986 | Baumann et al. |
| 4,592,755 A | 6/1986 | Penton |
| 4,608,396 A | 8/1986 | Baumann et al. |

(Continued)

FOREIGN PATENT DOCUMENTS

| | | |
|---|---|---|
| EP | 0230672 | 8/1987 |
| EP | 0315814 | 5/1989 |

(Continued)

OTHER PUBLICATIONS

Alvarez, Sonia et al, Synthesis of Macro/Mesoporous Silica and Carbon Monoliths By Using a Commercial Polyurethane Foam as Sacrificial Template, Material Letters, 2007, 2378-2381, 61.

(Continued)

*Primary Examiner* — Suzette J Gherbi
(74) *Attorney, Agent, or Firm* — Linda Fox

(57) ABSTRACT

Methods for breast reconstruction and augmentation are provided which may reduce the incidence of capsular contracture. Methods for treating an encapsulated breast and reducing potential for capsular contracture in the breast are also provided.

6 Claims, 1 Drawing Sheet

(56) References Cited

U.S. PATENT DOCUMENTS

| | | | |
|---|---|---|---|
| 4,610,690 A | 9/1986 | Tiffany | |
| 4,636,213 A | 1/1987 | Pakiam | |
| 4,643,733 A | 2/1987 | Becker | |
| 4,647,618 A | 3/1987 | Baumann et al. | |
| 4,648,880 A | 3/1987 | Brauman | |
| 4,650,487 A | 3/1987 | Chaglassian | |
| 4,651,717 A | 3/1987 | Jakubczak | |
| 4,681,587 A | 7/1987 | Eberl | |
| 4,740,208 A | 4/1988 | Cavon | |
| 4,772,285 A | 9/1988 | Ksander | |
| 4,773,908 A | 9/1988 | Becker | |
| 4,773,909 A | 9/1988 | Chaglassian | |
| 4,790,848 A | 12/1988 | Cronin | |
| 4,795,464 A | 1/1989 | Eberl | |
| 4,803,025 A | 2/1989 | Brockmeyer | |
| 4,828,560 A | 5/1989 | Heyler | |
| 4,840,628 A | 6/1989 | Cavon | |
| 4,841,992 A | 6/1989 | Sasaki | |
| 4,859,383 A | 8/1989 | Dillon | |
| 4,859,712 A | 8/1989 | Cox | |
| 4,889,744 A | 12/1989 | Quaid | |
| 4,899,764 A | 2/1990 | Gauger | |
| 4,902,294 A | 2/1990 | Gosserez | |
| 4,906,423 A | 3/1990 | Frisch | |
| 4,936,858 A | 6/1990 | O'Keeffe | |
| 4,944,749 A | 7/1990 | Becker | |
| 4,944,750 A | 7/1990 | Cox | |
| 4,950,292 A | 8/1990 | Audretsch | |
| 4,955,907 A | 9/1990 | Ledergerber | |
| 4,955,909 A | 9/1990 | Ersek | |
| 4,960,425 A | 10/1990 | Yan | |
| 4,965,430 A | 10/1990 | Curtis | |
| 4,969,899 A | 11/1990 | Cox | |
| 5,002,572 A | 3/1991 | Picha | |
| 5,007,929 A | 4/1991 | Quaid | |
| 5,007,940 A | 4/1991 | Berg | |
| 5,011,494 A | 4/1991 | von Recum et al. | |
| 5,022,942 A | 6/1991 | Yan | |
| 5,026,394 A | 6/1991 | Baker | |
| 5,034,422 A | 7/1991 | Triolo | |
| 5,035,249 A | 7/1991 | Sasaki | |
| 5,092,348 A * | 3/1992 | Dubrul et al. | 128/899 |
| 5,092,882 A | 3/1992 | Lynn | |
| 5,104,409 A | 4/1992 | Baker | |
| 5,116,387 A | 5/1992 | Berg | |
| 5,128,088 A | 7/1992 | Shirmomura et al. | |
| 5,135,959 A | 8/1992 | Hill | |
| 5,146,933 A | 9/1992 | Boyd | |
| 5,147,398 A | 9/1992 | Lynn | |
| 5,158,571 A | 10/1992 | Picha | |
| 5,158,573 A | 10/1992 | Berg | |
| 5,171,269 A | 12/1992 | Bark | |
| 5,185,297 A | 2/1993 | Park | |
| 5,207,709 A | 5/1993 | Picha | |
| 5,219,361 A | 6/1993 | von Recum et al. | |
| 5,236,453 A | 8/1993 | Picha | |
| 5,236,454 A | 8/1993 | Miller | |
| 5,236,457 A | 8/1993 | Devanathan | |
| 5,246,454 A | 9/1993 | Peterson | |
| 5,282,856 A | 2/1994 | Ledergerber | |
| 5,296,069 A | 3/1994 | Robert | |
| 5,348,788 A | 9/1994 | White | |
| 5,354,338 A | 10/1994 | Ledergerber | |
| 5,358,521 A | 10/1994 | Shane | |
| 5,376,117 A | 12/1994 | Pinchuk | |
| 5,383,929 A | 1/1995 | Ledergerber | |
| 5,437,824 A | 8/1995 | Carlisle | |
| 5,441,919 A | 8/1995 | Park | |
| 5,447,535 A | 9/1995 | Muller | |
| 5,455,100 A | 10/1995 | White | |
| 5,480,430 A | 1/1996 | Carlisle | |
| 5,496,367 A | 3/1996 | Fisher | |
| 5,496,370 A | 3/1996 | Hamas | |
| 5,507,808 A | 4/1996 | Becker | |
| 5,522,896 A | 6/1996 | Prescott | |
| 5,525,275 A | 6/1996 | Iversen | |
| 5,534,023 A | 7/1996 | Henley | |
| 5,545,217 A | 8/1996 | Offray | |
| 5,545,220 A * | 8/1996 | Andrews et al. | 623/8 |
| 5,549,671 A | 8/1996 | Waybright | |
| 5,571,179 A | 11/1996 | Manders | |
| 5,589,176 A | 12/1996 | Seare | |
| 5,605,693 A | 2/1997 | Seare | |
| 5,607,473 A | 3/1997 | Weber-Unger | |
| 5,624,674 A | 4/1997 | Seare | |
| 5,630,843 A | 5/1997 | Rosenberg | |
| 5,630,844 A | 5/1997 | Dogan | |
| 5,653,755 A | 8/1997 | Ledergerber | |
| 5,658,330 A | 8/1997 | Carlisle | |
| 5,674,285 A | 10/1997 | Quaid | |
| 5,681,572 A | 10/1997 | Seare | |
| 5,776,159 A | 7/1998 | Young | |
| 5,779,734 A | 7/1998 | Ledergerber | |
| 5,798,065 A | 8/1998 | Picha | |
| 5,824,081 A | 10/1998 | Knapp | |
| 5,843,189 A | 12/1998 | Perouse | |
| 5,855,588 A | 1/1999 | Young | |
| 5,871,497 A | 2/1999 | Young | |
| 5,895,423 A | 4/1999 | Becker | |
| 5,935,164 A | 8/1999 | Iversen | |
| 5,961,552 A | 10/1999 | Iversen | |
| 5,964,803 A | 10/1999 | Iversen | |
| 5,965,076 A | 10/1999 | Banks | |
| 5,984,943 A | 11/1999 | Young | |
| 5,993,716 A | 11/1999 | Draenert | |
| 6,071,309 A | 6/2000 | Knowlton | |
| 6,074,421 A | 6/2000 | Murphy | |
| 6,083,262 A | 7/2000 | Caravel | |
| 6,099,565 A | 8/2000 | Sakura | |
| 6,113,634 A | 9/2000 | Weber-Unger | |
| 6,146,418 A | 11/2000 | Berman | |
| 6,183,514 B1 | 2/2001 | Becker | |
| 6,187,043 B1 | 2/2001 | Ledergerber | |
| 6,203,570 B1 | 3/2001 | Baeke | |
| 6,206,930 B1 | 3/2001 | Burg | |
| 6,214,045 B1 | 4/2001 | Corbitt | |
| 6,214,926 B1 | 4/2001 | Winn | |
| 6,315,796 B1 | 11/2001 | Eaton | |
| 6,340,648 B1 | 1/2002 | Imura et al. | |
| 6,387,133 B1 | 5/2002 | Perouse | |
| 6,432,138 B1 | 8/2002 | Offray | |
| 6,464,726 B1 | 10/2002 | Heljenek | |
| 6,520,989 B1 | 2/2003 | Eaton | |
| 6,531,523 B1 | 3/2003 | Davankov | |
| 6,544,287 B1 | 4/2003 | Johnson | |
| 6,602,452 B2 | 8/2003 | Schuessler | |
| 6,605,116 B2 | 8/2003 | Falcon | |
| 6,638,308 B2 | 10/2003 | Corbitt | |
| 6,673,285 B2 | 1/2004 | Ma | |
| 6,692,527 B1 | 2/2004 | Bellin | |
| 6,755,861 B2 | 6/2004 | Nakao | |
| 6,802,861 B1 | 10/2004 | Hamas | |
| 6,811,570 B1 | 11/2004 | Gehl | |
| 6,818,673 B2 | 11/2004 | Ferguson | |
| 6,875,233 B1 | 4/2005 | Turner | |
| 6,881,226 B2 | 4/2005 | Corbitt | |
| 6,900,055 B1 | 5/2005 | Fuller | |
| 6,913,626 B2 | 7/2005 | McGhan | |
| 6,916,339 B1 | 7/2005 | Missana | |
| 6,921,418 B2 | 7/2005 | Ledergerber | |
| 6,932,840 B1 | 8/2005 | Bretz | |
| 7,081,135 B2 | 7/2006 | Smith | |
| 7,081,136 B1 | 7/2006 | Becker | |
| 7,105,116 B2 | 9/2006 | Bellin | |
| 7,169,180 B2 | 1/2007 | Brennan | |
| 7,192,450 B2 | 3/2007 | Brauker | |
| 7,244,270 B2 | 7/2007 | Lesh | |
| 7,323,208 B2 | 1/2008 | Ma | |
| 7,476,249 B2 | 1/2009 | Frank | |
| 7,520,896 B2 | 4/2009 | Benslimane | |
| 7,547,393 B2 | 6/2009 | Ramaswamy | |
| 7,625,405 B2 | 12/2009 | Purkait | |
| 7,632,228 B2 | 12/2009 | Brauker | |
| 7,632,291 B2 | 12/2009 | Stephens | |

(56) References Cited

U.S. PATENT DOCUMENTS

| | | |
|---|---|---|
| 7,641,688 B2 | 1/2010 | Lesh |
| 7,645,475 B2 | 1/2010 | Prewett |
| 8,202,317 B2 | 6/2012 | Becker |
| 8,313,527 B2 | 11/2012 | Powell et al. |
| 8,487,012 B2 | 7/2013 | Goraltchouk et al. |
| 2002/0038147 A1 | 3/2002 | Miller |
| 2002/0193885 A1 | 12/2002 | Legeay |
| 2003/0036803 A1 | 2/2003 | McGhan |
| 2003/0093151 A1 | 5/2003 | Zhang |
| 2003/0105469 A1 | 6/2003 | Karmon |
| 2003/0205846 A1 | 11/2003 | Bellin |
| 2003/0208269 A1 | 11/2003 | Eaton |
| 2004/0010225 A1 | 1/2004 | Schuessler |
| 2004/0115241 A1 | 6/2004 | Calhoun |
| 2004/0127985 A1 | 7/2004 | Bellin |
| 2004/0143327 A1 | 7/2004 | Ku |
| 2004/0148024 A1 | 7/2004 | Williams |
| 2004/0153151 A1 | 8/2004 | Gonzales de Vicente |
| 2004/0176493 A1 | 9/2004 | Ferguson |
| 2004/0213986 A1 | 10/2004 | Kim |
| 2005/0055093 A1 | 3/2005 | Brennan |
| 2005/0070124 A1 | 3/2005 | Miller |
| 2005/0122169 A1 | 6/2005 | Watanabe |
| 2005/0196452 A1 | 9/2005 | Boyan |
| 2005/0216094 A1 | 9/2005 | Prewett |
| 2005/0251083 A1 | 11/2005 | Carr-Brendel et al. |
| 2006/0002810 A1 | 1/2006 | Grohowski |
| 2006/0036266 A1 | 2/2006 | Sulamanidze et al. |
| 2006/0036320 A1 | 2/2006 | Job |
| 2006/0136056 A1 | 6/2006 | Wohl |
| 2006/0224239 A1 | 10/2006 | Tiahrt |
| 2006/0229721 A1 | 10/2006 | Ku |
| 2006/0235094 A1 | 10/2006 | Habibi-Naini |
| 2006/0246121 A1 | 11/2006 | Ma |
| 2007/0093911 A1 | 4/2007 | Fricke |
| 2007/0104693 A1 | 5/2007 | Quijano |
| 2007/0104695 A1 | 5/2007 | Quijano |
| 2007/0116735 A1 | 5/2007 | Calhoun |
| 2007/0135916 A1 | 6/2007 | Maxwell |
| 2007/0154525 A1 | 7/2007 | Calhoun |
| 2007/0190108 A1 | 8/2007 | Datta |
| 2007/0198085 A1 | 8/2007 | Benslimane |
| 2008/0009830 A1 | 1/2008 | Fujimoto |
| 2008/0071371 A1 | 3/2008 | Elshout |
| 2008/0075752 A1 | 3/2008 | Ratner |
| 2008/0154366 A1 | 6/2008 | Frank |
| 2008/0241212 A1 | 10/2008 | Moses |
| 2008/0268019 A1 | 10/2008 | Badylak |
| 2008/0312739 A1 | 12/2008 | Agerup |
| 2009/0045166 A1 | 2/2009 | Li |
| 2009/0082864 A1 | 3/2009 | Chen |
| 2009/0087641 A1 | 4/2009 | Favis |
| 2009/0093878 A1 | 4/2009 | Glicksman |
| 2009/0118829 A1 | 5/2009 | Powell |
| 2009/0125107 A1 | 5/2009 | Maxwell |
| 2009/0148829 A1 | 6/2009 | Ecker |
| 2009/0169716 A1 | 7/2009 | Linhardt |
| 2009/0198331 A1 | 8/2009 | Kesten |
| 2009/0198332 A1 | 8/2009 | Becker |
| 2009/0198333 A1 | 8/2009 | Becker |
| 2010/0042211 A1 | 2/2010 | Van Epps et al. |
| 2010/0042212 A1 | 2/2010 | Van Epps et al. |
| 2010/0292790 A1 | 11/2010 | Stroumpulis et al. |
| 2011/0035004 A1 | 2/2011 | Maxwell |
| 2011/0054605 A1 | 3/2011 | Becker |
| 2011/0093069 A1 | 4/2011 | Goraltchouk et al. |
| 2011/0106249 A1 | 5/2011 | Becker |
| 2011/0117267 A1 | 5/2011 | Powell et al. |
| 2011/0196488 A1 | 8/2011 | Goraltchouk et al. |
| 2011/0196489 A1 | 8/2011 | Van Epps et al. |
| 2011/0276133 A1 | 11/2011 | Liu et al. |
| 2011/0276134 A1 | 11/2011 | Manesis et al. |
| 2011/0278755 A1 | 11/2011 | Liu et al. |
| 2011/0282444 A1 | 11/2011 | Liu et al. |
| 2011/0309541 A1 | 12/2011 | Thompson et al. |
| 2011/0313073 A1 | 12/2011 | Goraltchouk et al. |
| 2012/0004722 A1 | 1/2012 | Goraltchouk et al. |
| 2012/0041555 A1 | 2/2012 | Manesis et al. |
| 2012/0077010 A1 | 3/2012 | Manesis et al. |
| 2012/0077012 A1* | 3/2012 | Liu et al. ............... 428/221 |
| 2012/0077891 A1 | 3/2012 | Liu et al. |
| 2012/0101574 A1 | 4/2012 | Goraltchouk et al. |
| 2012/0142798 A1 | 6/2012 | Thompson et al. |
| 2012/0148632 A1 | 6/2012 | Chan et al. |
| 2012/0226352 A1* | 9/2012 | Becker ........................ 623/8 |
| 2012/0245685 A1 | 9/2012 | Yu |
| 2012/0321777 A1 | 12/2012 | Stroumpoulis et al. |
| 2013/0006279 A1* | 1/2013 | Mortarino .............. 606/151 |
| 2013/0013062 A1 | 1/2013 | Thompson et al. |
| 2013/0018393 A1* | 1/2013 | Bengtson ............... 606/144 |
| 2013/0023987 A1 | 1/2013 | Liu et al. |
| 2013/0032962 A1 | 2/2013 | Liu et al. |
| 2013/0053956 A1 | 2/2013 | Powell et al. |
| 2013/0317610 A1* | 11/2013 | Ledergerber ................ 623/8 |

FOREIGN PATENT DOCUMENTS

| | | |
|---|---|---|
| EP | 0522585 | 1/1993 |
| EP | 1532942 | 5/2005 |
| FR | 2840617 | 12/2003 |
| JP | 2003-062062 | 4/2003 |
| JP | 2007-029717 | 8/2007 |
| WO | 98-10803 | 3/1998 |
| WO | 00-24437 | 5/2000 |
| WO | 2004-037318 | 5/2004 |
| WO | 2004-062531 | 7/2004 |
| WO | 2006-133366 | 12/2006 |
| WO | 2008/100534 | 8/2008 |
| WO | 2009-061672 | 5/2009 |
| WO | 2009-110917 | 9/2009 |
| WO | WO 2010074827 A2 * | 7/2010 |
| WO | 2011-094155 | 8/2011 |
| WO | 2011-097499 | 8/2011 |

OTHER PUBLICATIONS

Barnsley, Philip et al, Textured Surface Breast Implants in the Prevention of Capsular Contracture Among Breast Augmentation Patients: A Meta-Analysis of Randomized Controlled Trials, Plastic and Reconstructive Surgery, 2006, 2182-2190, 117(7).

Barr, S., Current Implant Surface Technology: An Examination of Their Nanostructure and Their Influence on Fibroblast Alignment and Biocompatibility, J. of Plastic Surgery, 2009, 198-217, 9.

Brauker, James et al, Neovascularization of Synthetic Membranes Directed By Membrane Microarchitecture, Journal of Biomedical Materials Research, 1995, 1517-1524, 29, John Wiley & Sons, Inc.

Brohim, Robert et al, Early Tissue Reaction to Textured Breast Implant Surfaces, Ann Plast Surg, 1992, 354-362, 28.

Inamed Aesthetics Brochure, Directions for Use Style 410 Silicone-Filled Breast Implants (2003).

Ma, Peter, Scaffolds for Tissue Fabriction, Materials Today, 2004, 30-40, 7.

Mikos, Antonios, Formation of Highly Porous Biodegradable Scaffolds For Tissue Engineering, Journal of Biotechnology, Aug. 15, 2000, 114-119, 3(2).

Minami, Eliza, The Composition and Behavior of Capsules Around Smooth and Textured Breast Implants in Pigs, Plast. Reconstr. Surg., 2006, 874-884, 118.

Murphy, William L. et al., Salt Fusion: An Approach To Improve Pore Interconnectivity Within Tissue Engineering Scaffolds, Tissue Engineering, 2002, 43-52, 8 (1), US.

Sharkawy, A. Adam, Engineering the Tissue Which Encapsulates Subcutaneous Implants. II. Plasma-tissue Exchange Properties, John Wiley & Sons, 1998, 586-597.

Wei, Guobao et al, Macroporous and Nanofibrous Polymer Scaffolds and Polymer/Bone-Like Apatite Composite Scaffolds Generated by Sugar Spheres, Journal of Biomedical Materials Research, 2006, 306-315, 78A.

Zhang, Yuan, Macroporous Alumina Monoliths Prepared by Filling Polymer Foams with Alumina Hydrosels, Journal of Materials Science, 2009, 931-938, 44, Springer Science.

(56) References Cited

OTHER PUBLICATIONS

Abramo, AC., De Oliveira, VR., Ledo-Silva, MC., De Oliveira, EL. How texture-inducing contraction vectors affect the fibrous capsule shrinkage around breasts implants? Aesthetic Plast Surg. 2010;34:555-560.

Adams, WP, Jr. Capsular contracture: what is it? What causes it? How can it be prevented and managed? Clin Plast Surg. 2009;36:119-26, vii.

Asplund, O., Gylbert, L., Jurell, G., Ward, C. Textured or smooth implants for submuscular breast augmentation: A controlled study. Plast Reconstr Surg. 1996;97:1200-1206.

Baker, JL, Jr.., Chandler, ML., LeVier, RR. Occurrence and activity of myofibroblasts in human capsular tissue surrounding mammary implants. Plast Reconstr Surg. 1981;68:905-912.

Barnsley, GP., Sigurdson, LJ., Barnsley, SE. Textured surface breast implants in the prevention of capsular contracture among breast augmentation patients: a meta-analysis of randomized controlled trials. Plast Reconstr Surg. 2006;117:2182-2190.

Batra, M., Bernard, S., Picha, G. Histologic comparison of breast implant shells with smooth, foam, and pillar microstructuring in a rat model from 1 day to 6 months. Plast Reconstr Surg. 1995;95:354-363.

Brohim, RM., Foresman, PA., Hildebrandt, PK., Rodeheaver, GT. Early tissue reaction to textured breast implant surfaces. Ann Plast Surg. 1992;28:354-362.

Coleman, DJ., Foo, IT., Sharpe, DT. Textured or smooth implants for breast augmentation? A prospective controlled trial. Br J Plast Surg. 1991;44:444-448.

Coleman, DJ., Sharpe, DT., Naylor, IL., Chander, CL., Cross, SE. The role of the contractile fibroblast in the capsules around tissue expanders and implants. Br J Plast Surg. 1993;46:547-556.

Collis, N., Coleman, D., Foo, IT., Sharpe, DT. Ten-year review of a prospective randomized controlled trial of textured versus smooth subglandular silicone gel breast implants. Plast Reconstr Surg. 2000;106:786-791.

Darby, I., Skalli, O., Gabbiani, G. Alpha-smooth muscle actin is transiently expressed by myofibroblasts during experimental wound healing. Lab Invest. 1990;63:21-29.

del Rosario, AD., Bui, HX., Petrocine, S., Sheehan, C., Pastore, J., Singh, J., Ross, JS. True synovial metaplasia of breast implant capsules: A light and electron microscopic study. Ultrastruct Pathol. 1995;19:83-93.

Hakelius, L., Ohlsen, L. A clinical comparison of the tendency to capsular contracture between smooth and textured gel-filled silicone mammary implants. Plast Reconstr Surg. 1992;90:247-254.

Hakelius, L., Ohlsen, L. Tendency to capsular contracture around smooth and textured gel-filled silicone mammary implants: A five-year follow-up. Plast Reconstr Surg. 1997;100:1566-1569.

Hameed, MR., Erlandson, R., Rosen, PP. Capsular synovial-like hyperplasia around mammary implants similar to detritic synovitis: A morphologic and immunohistochemical study of 15 cases. Am J Surg Pathol. 1995;19:433-438.

Henriksen, TF., Fryzek, JP., Holmich, LR., McLaughlin, JK., Kjoller, K., Hoyer, AP., Olsen, JH., Friis, S. Surgical intervention and capsular contracture after breast augmentation: A prospective study of risk factors. Ann Plast Surg. 2005;54:343-351.

Hwang, K., Sim, HB., Huan, F., Kim, DJ. Myofibroblasts and capsular tissue tension in breast capsular contracture. Aesthetic Plast Surg. 2010;34:716-721.

Joseph, J., Mohanty, M., Mohanan, PV. Role of immune cells and inflammatory cytokines in regulation of fibrosis around silicone expander implants. J Mater Sci Mater Med. 2010;21:1665-1676.

Kamel, M., Protzner, K., Fornasier, V., Peters, W., Smith, D., Ibanez, D. The peri-implant breast capsule: An immunophenotypic study of capsules taken at explantation surgery. J Biomed Mater Res. 2001;58:88-96.

Ko, CY., Ahn, CY., Ko, J., Chopra, W., Shaw, WW. Capsular synovial metaplasia as a common response to both textured and smooth implants. Plast Reconstr Surg. 1996;97:1427-1433.

Lossing, C., Hansson, HA. Peptide growth factors and myofibroblasts in capsules around human breast implants. Plast Reconstr Surg. 1993;91:1277-1286.

Pajkos, A., Deva, AK., Vickery, K., Cope, C., Chang, L., Cossart, YE. Detection of subclinical infection in significant breast implant capsules. Plast Reconstr Surg. 2003;111:1605-1611.

Powell, DW. Myofibroblasts: Paracrine cells important in health and disease. Trans Am Clin Climatol Assoc. 2000;111:271-292.

Prantl, L., Poppl, N., Horvat, N., Heine, N., Eisenmann-Klein, M. Serologic and histologic findings in patients with capsular contracture after breast augmentation with smooth silicone gel implants: Is serum hyaluronan a potential predictor? Aesthetic Plast Surg. 2005;29:510-518.

Prantl, L., Schreml, S., Fichtner-Feigl, S., Poppl, N., Eisenmann-Klein, M., Schwarze, H., Fuchtmeier, B. Clinical and morphological conditions in capsular contracture formed around silicone breast implants. Plast Reconstr Surg. 2007;120:275-284.

Raso, DS., Schulte, BA. Immunolocalization of keratan sulfate, chondroitin-4-sulfate, and chondroitin-6-sulfate in periprosthetic breast capsules exhibiting synovial metaplasia. Plast Reconstr Surg. 1996;98:78-82.

Rohrich, RJ., Kenkel, JM., Adams, WP. Preventing capsular contracture in breast augmentation: In search of the Holy Grail. Plast Reconstr Surg. 1999;103:1759-1760.

Rubino, C., Mazzarello, V., Farace, F., D'Andrea, F., Montella, A., Fenu, G., Campus, GV. Ultrastructural anatomy of contracted capsules around textured implants in augmented breasts. Ann Plast Surg. 2001;46:95-102.

Rudolph, R., Abraham, J., Vecchione, T., Guber, S., Woodward, M. Myofibroblasts and free silicon around breast implants. Plast Reconstr Surg. 1978;62:185-196.

Siggelkow, W., Faridi, A., Spiritus, K., Klinge, U., Rath, W., Klosterhalfen, B. Histological analysis of silicone breast implant capsules and correlation with capsular contracture. Biomaterials. 2003;24:1101-1109.

Skalli, O., Ropraz, P., Trzeciak, A., Benzonana, G., Gillessen, D., Gabbiani, G. A monoclonal antibody against alpha-smooth muscle actin: A new probe for smooth muscle differentiation. J Cell Biol. 1986;103:2787-2796.

Wyatt, LE., Sinow, JD., Wollman, JS., Sami, DA., Miller, TA. The influence of time on human breast capsule histology: Smooth and textured silicone-surfaced implants. Plast Reconstr Surg. 1998;102:1922-1931.

Ayres et al., "Modulation of anistropy in electrospun tissue-engineering scaffolds: Analysis of fiber alignment by the fast Fourier transform", Biomaterials 27 (2006) 5524-5534.

* cited by examiner

SURGICAL METHODS FOR BREAST RECONSTRUCTION OR AUGMENTATION

BACKGROUND

The present invention generally relates to surgical methods, and more specifically relates to breast augmentation, reconstruction and breast implant revision surgical methods.

Prostheses or implants for augmentation and/or reconstruction of the human body are well known. Capsular contracture is a complication associated with surgical implantation of prostheses, particularly with soft implants, and even more particularly, though certainly not exclusively, with fluid-filled breast implants.

When a foreign material is implanted in a human body, the immune system attempts to isolate the material by forming a collagen-based capsule. After time, the capsule may contract, becoming hardened and painful, and possibly requiring surgical correction. This phenomenon is known as "capsular contracture" and is a significant adverse event for breast implant patients.

Capsular contracture is believed to be a result of the immune system response to the presence of a foreign material in the body. A normal response of the body to the presence of a newly implanted object, for example a breast implant, is to form a capsule of tissue, primarily collagen fibers, around the implant. Capsular contracture occurs when the capsule begins to contract and squeeze the implant. This contracture can be discomforting or even extremely painful, and can cause distortion of the augmented or reconstructed breast. The exact cause of contracture is not known. However, some factors may include bacterial contamination of the implant prior to or after placement, submuscular versus subgladular placement, and smooth surface implants versus textured surface implants, and bleeding, pocket size or trauma to the area. It is also known that contracture rates are increased in patients following an implant replacement after removal for an initial contracture as well as in patients undergoing breast reconstruction following mastectomy or radiation therapy for breast cancer.

A conventional procedure for treating a contracted capsule is known as a capsulectomy, in which capsular tissue is removed from the breast either with the implant or following removal of the implant. This is generally performed once contracture has reached a severity which considerably affects the look and feel of the breast or causes significant discomfort to the patient. The procedure involves gaining entry to the breast interior by way of a surgical incision and removing the implant and the entire capsule of fibrous tissue surrounding the implant. Most commonly, this capsule is removed whole, to eliminate the chance of a recurrence. Capsule removal is an invasive procedure which involves removal of healthy tissue from the already compromised breast, as it is a goal to remove all of fibrous capsule tissue. Most often, because of the significant loss of tissue, a new implant must be introduced into the breast cavity. When a patient has thin tissue and not sufficient breast tissue and/or breast glandular tissue, removing the capsular tissue can result in severe deficiency of remaining breast tissue, which may lead to severe rippling, visibility and possibly even skin necrosis due to poor blood supply, when the new implant is placed. In some cases the capsule is not entirely removed following explantation of the implant, but is surgically scored to release the tension of the contracted capsule.

There is still a need for better methods for reducing the occurrence or reoccurance of capsular contracture in patients receiving breast implants.

SUMMARY

Surgical methods and devices are provided for breast reconstruction and augmentation which reduced potential for capsular contracture.

In accordance with one aspect of the invention a method for augmenting/reconstructing a breast in a patient generally comprises the steps of introducing a first prosthesis having a first surface texture into a breast, and allowing the first prosthesis to remain in the breast for a time sufficient for a tissue capsule to form about the first prosthesis. The first prosthesis is then removed from the breast to form a breast cavity.

A second prosthesis, having a second surface texture is then introduced into the breast cavity and the preexisting tissue capsule is disrupted and reduced in severity over time. In one aspect of the invention, the second surface texture has a structure which stimulates tissue integration from preformed capsular tissue. In some instances, the second surface texture may be a non-bioresorbable surface, for example, a porous silicone elastomeric surface having a highly interconnected, open-celled structure.

In one aspect of the invention, the second surface texture has a texture different from the first surface texture. The first surface texture may differ from the second surface texture in terms of average pore size, pore interconnectivity, pore density and/or any and other structural distinction which will result in disruption of capsular tissue formed adjacent the first texture.

For example, in some embodiments, the first surface texture may have a relatively small average pore size and/or with pores lacking interconnectivity between pores, for example, the pores being only open to the outside or, alternatively, the first surface texture may have no significant pores at all. In this case, the second surface texture may have relatively larger average pore size and/or greater interconnectivity between pores, for example, pores which generally connect with each other below the surface of on the implant, for example, pores forming something of a honeycomb-like structure.

For example, in some embodiments, the first implant may be relatively smooth or have an average pore size of no greater than about 200 µm to about 500 µm, and the average pore size of the second surface texture is greater than about 600 µm with pores interconnecting with each other allowing for tissue integration and connectivity between pores.

The first prosthesis may be an inflatable prosthesis, for example, a conventional, inflatable tissue expander. Such inflatable prostheses often include a port and tubing, or other structure for facilitating inflation of the implant in situ. The first prosthesis may be inflated over a period of time to allow for tissue expansion, prior to the step of removing the tissue expander. The first prosthesis is left in place until such time as a capsule forms about the surface of the prosthesis. In some embodiments, the prosthesis remains in place for a period of weeks or months, for example, between about 4 weeks and about 6 months.

The second prosthesis may be a conventional breast implant, for example, a prosthesis intended as a "permanent" implant. The second prosthesis may be a fillable, inflatable breast implant, or a silicone gel filled breast implant. The second prosthesis is implanted into the capsule remaining in the breast after removal of the first prosthesis.

In another aspect of the invention, a device useful for treating capsular contracture in a breast is provided wherein the device comprises a breast implant having a textured surface that, when implanted into a breast cavity defined by a preformed, intact, organized collagen capsule, results in remodeling and/or disruption of the preformed intact collagen capsule to result in a softer, less organized capsule less likely to contract had the primary implant been left in place. The textured surface of the device is, in some embodiments, a non-bioresorbable porous silicone surface defined by open-celled, interconnected pores having an average pore size of at least about 400 µm, for example, at least about 500 µm, for example, greater than about 600 µm, or larger.

BRIEF DESCRIPTION OF THE DRAWINGS

The invention may be more readily understood and appreciated with reference to the following Detailed Description when considered in conjunction with the accompanying Drawings of which.

DETAILED DESCRIPTION

Figure 1A:
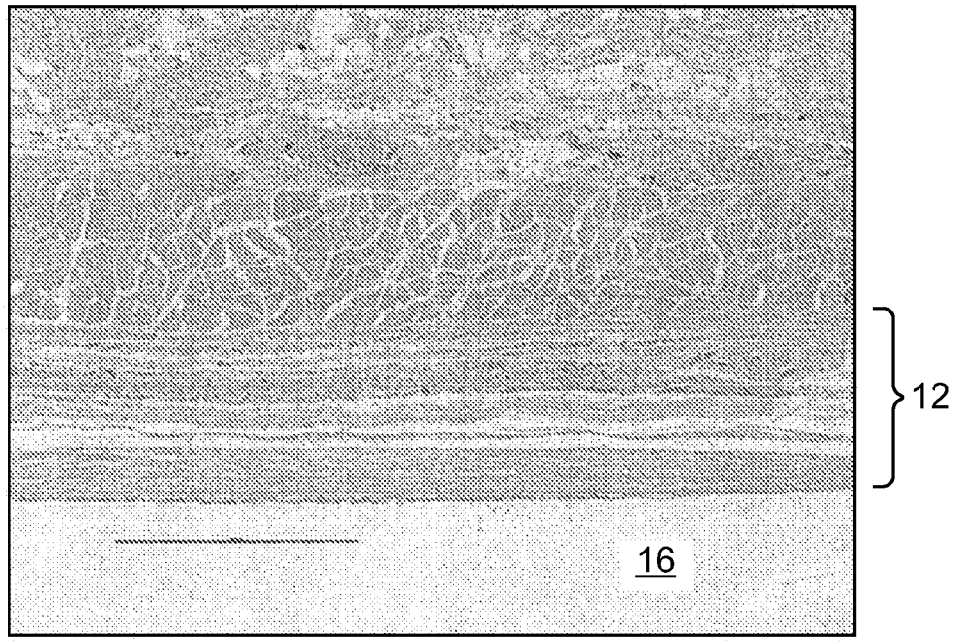
FIG. 1A is a 5× image taken from an intact, capsule of a male Sprague-Dawley rat, the capsule having been formed about a smooth surface primary implant.

In a broad aspect of the invention, methods are provided for reconstructing or augmenting a breast in a human patient, wherein the methods result in reduced occurrence of capsular contracture relative to conventional methods or of providing a surface structure which stimulates the remodeling of the pre-existing capsule to a less surface aligned collagen capsule structure less prone to contracture.

The present methods are useful in various breast surgical settings, including primary reconstruction procedures, e.g. the replacement of breast tissues damaged by trauma, disease (for example, breast cancer), and failed anatomic development (tuberous breast deformity); revision and reconstruction procedures, e.g. the revision or correction of a previous breast reconstruction surgery; and primary augmentation procedures, e.g. aesthetic augmentation to change the size, form, and feel of the breasts.

In an exemplary embodiment, the methods generally comprise the steps of introducing a first prosthesis, for example, a tissue expander, having a first surface texture, into a breast and forming a breast cavity of a desired volume by inflating the tissue expander while in the breast. The first prosthesis is removed from the breast and a second prosthesis, having a second texture different from the first texture, is implanted into the breast cavity.

For the sake of simplicity, the present disclosure will generally refer to the first prosthesis as a tissue expander or primary implant, temporary prosthesis, or temporary breast implant based on a planned or medically required removal, and the second prosthesis as a breast implant or permanent breast implant; however, it must be appreciated that the present invention is not limited to this particular combination.

If the device is a tissue expander or primary implant, it is left to remain in the breast for a sufficient length of time to expand the tissue surrounding the tissue expander. The inflation may be accomplished by incrementally and gradually inflating the expander over a period of time, for example a period of weeks or months, as is conventional in the field of breast reconstructive surgical procedures, to allow safe, gradual growth of tissue and enlargement of the pocket or cavity to be formed upon removal of the tissue expander.

In some breast augmentation/reconstruction procedures, a deflated, rolled tissue expander is positioned in either the subglandular or subpectoral position and the tissue expander is inflated by introducing a suitable inflation medium, such as saline solution for example, through a tissue expander inflation lumen into the interior of the tissue expander. The tissue expander is then filled with a sufficient amount of fluid to cause the tissue expander to expand the tissue and create the desired pocket for the second prosthesis, for example, a permanent implant.

In some embodiments, the tissue expander is inflated to a size about equivalent to the size of the expected permanent prosthesis. In other embodiment, the tissue expander is inflated to a size somewhat larger than the expected permanent prosthesis size in order to cause the tissue expander to create a pocket large enough to accommodate the second implant. By way of example, if a 400 cc permanent implant is desired to be placed, the tissue expander may be inflated to 500 cc to 700 cc or greater to assure that the tissue expander dissects the plane all the way to the margin defined in all directions by the circumferential mammary ligament.

In one embodiment of the invention, the tissue expander is allowed to remain in the body long enough to expand the space and create a sufficient pocket for the subsequent device implant. This may take a period of 4 weeks or more, for example, 6 weeks, 10 weeks, 12 weeks or 16 weeks. For example, the expander is left in place and gradually expands the dissected tissue pocket. That is, the tissue expander is periodically filled further to cause tissue to propagate thereby creating a larger space. The expander is left in place for the amount of time required to achieve a sufficient pocket. During this time a capsule is formed around the tissue expander.

Once the desired pocket size is achieved, the tissue expander is surgically removed from the breast. The capsule is generally formed of well-organized, fibrous collagen tissue interfacing and sometimes integrated into the external surfaces of the expander. Removal of the expander leaves a breast cavity, or pocket, defined by the tissue capsule. In some instances, a partial capsulectomy is performed, removing a portion of the capsule when the expander is removed from the breast. In other instances, the surgeon leaves as much of the capsule intact as possible.

After removal of the expander, a breast prosthesis is then introduced into the breast cavity, for example, into the tissue capsule that was formed about the tissue expander. The breast prosthesis has a second surface texture that is different from the texture of the tissue expander. For example, the first prosthesis, e.g. tissue expander, may have a first texture defined by or characterized by a smooth surface, or a closed cell silicone surface (pores open on one side to the outside) having an average pore size of between about 200 µm and about 500 µm, and the second prosthesis may have second texture defined by or characterized by a an interconnected open-celled silicone surface having an average pore size of greater than 500 to 600 µm.

After being implanted into the breast cavity defined by the intact capsular tissue with characteristic highly aligned collagen fibers, the second surface texture causes a significant change in the existing capsular tissue resulting in tissue ingrowth into the prosthesis and disruption of the previous collagen fiber alignment around the circumference of the implant. For example a clinically significant change occurs in the preexisting capsular tissue, in that the highly aligned collagen fibers of preexisting capsule that were adjacent to the implant become less aligned and parallel to the circumference of the implant and therefore are less likely to contract exert forces leading to constriction of the implant and hardening of the implant over time. "Remodeled" capsular tissue is defined herein as organized, preexisting capsular tissue which has, over time, become less organized, for example, contains less linearly aligned and organized collagen fibers encircling the implant, and has become more cellular relative to the preexisting capsule structure. Such a remodeled capsule is softer, more integrated with the implant surface, and has a reduced potential for capsular contracture. Such remodeling of capsular tissue may be in the form of enhanced tissue ingrowth of newly formed cells and collagen fibers into the second prosthesis surface.

In another aspect, methods are provided for reducing, disrupting or otherwise ameliorating the severity of a pre-existing, organized capsule surrounding an implant, for example a smooth or moderately textured permanent prosthesis. For example, in some embodiments the invention, the methods comprise treating capsular contracture in a breast having an original implant by removing the original implant leaving at least some of the contracted tissue in place in the body and implanting a new implant having a texture effective at stimulating the remodeling of the existing capsule structure.

After a mature capsule has developed, the implant is surgically removed through an incision, and a replacement prosthesis is placed inside the pre-existing capsule. The incision is closed such that the implant is positioned inside the pocket created by the pre-existing capsule. The new, replacement prosthesis has an interconnected, open-cell surface texture which stimulates remodeling of the capsule, forming a less severe, more integrated remodeled capsule about the new implant having a disorganized collagen structure less likely to result in contracture relative the original capsule. Other advantages of the remodeled capsule include a softer-feeling implant and reduced need for capsulectomy (capsule removal) or capsulotomy (capsule scoring) following explanation of the first implant.

In another aspect of the invention, a device useful for treating capsular contracture in a breast is provided, wherein the device comprises a breast implant, for example, a silicone gel filled or saline filled inflatable breast implant, having a textured surface that, when implanted into a breast cavity defined by a preformed, intact, organized collagen capsule, results in remodeling and/or disruption of the preformed intact collagen capsule to result in a softer, less organized capsule less likely to contract had the primary implant been left in place. The textured surface of the device is, in some embodiments, a non-bioresorbable porous silicone surface defined by open-celled, interconnected pores. In some embodiments, the average pore size of the textured surface is between about 400 μm to about 800 μm, or greater, for example, up to about 1.0 mm, or greater. The pores are preferably highly interconnected and/or include other structure for promoting cell ingrowth and disruption of alignment of collagen fibers over time. In a specific embodiment, the textured surface has an average pore size of greater than about 600 μm.

Remodeling the pre-existing capsule, with organized collagen fibers, to a softer, disorganized collagen fiber structure may be achieved with an interconnected open-cell texture implant described in certain commonly-owned patent applications, and/or made by by a variety of methods, for example, such as those devices and methods disclosed in commonly-owned U.S. patent application Ser. No. 13/104,811, filed 10 May 2011, U.S. patent application Ser. No. 13/246,568, filed 27 Sep. 2011, U.S. patent application Ser. No. 13/104,888, filed 10 May 2011, U.S. patent application Ser. No. 13/104, 395, filed 10 May 2011, and U.S. patent application Ser. No. 13/247,835, filed 30 Sep. 2011, the entire disclosure of each of these applications being incorporated herein by this specific reference.

EXAMPLE 1A

Capsule Formation in a Laboratory Animal

A male Sprague-Dawley rat, approximately 250 g, was implanted with a smooth textured mini-tissue expander along the dorsal surface. The tissue expander was inflated to 6 ml. After 6 weeks, the implant and the surrounding tissue were removed, processed and stained with hematoxylin and eosin to identify gross tissue morphology. FIG. 1A is a 5× image of intact capsule tissue formed about the mini-tissue expander taken from the rat. The capsule tissue 12 can be clearly seen in this picture as a smooth, thick band of collagen fibers adjacent the tissue expander 16. The capsule is composed mainly of parallel, organized collagen fibers. If left to remain in place, highly organized fibrous capsules such as the one shown in FIG. 1A, have greater potential to become contracted and hardened over time, relative to less organized, more integrated capsules such as the "remodeled" capsule shown in FIG. 1B and described in the following Example 1B.

EXAMPLE 1B

Preexisting Capsule Remodeling in a Laboratory Animal

Figure 1B:
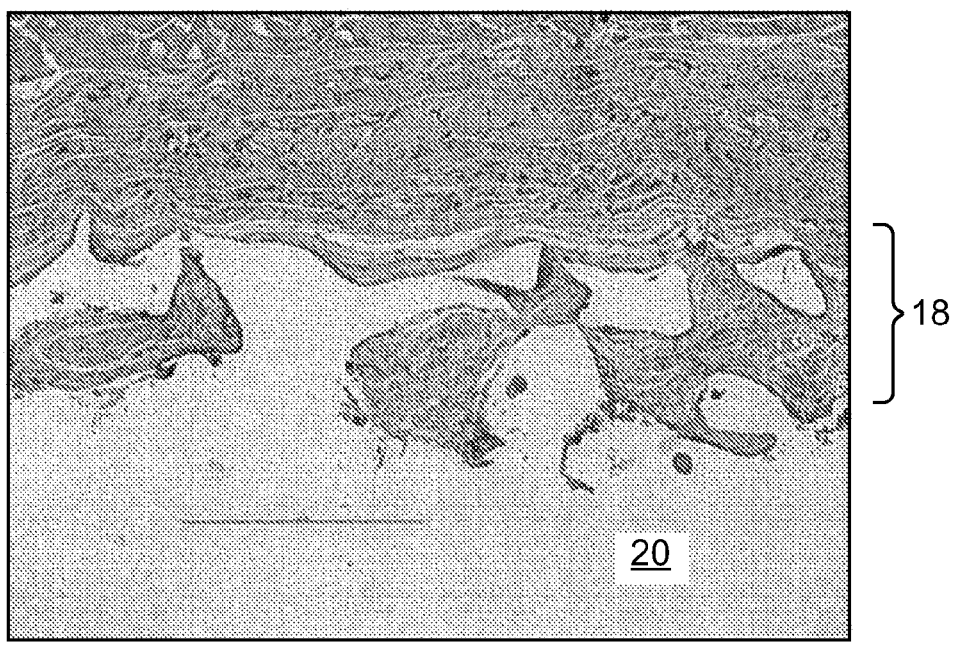
FIG. 1B is a 5× image taken from a capsule of a male Sprague-Dawley rat, the capsule having been "remodeled" and less likely to contract, using methods and devices of the present invention.

A male Sprague-Dawley rat, approximately 250 g, was implanted with a smooth textured mini-tissue expander along the dorsal surface, as in Example 1A. The mini-tissue expander was inflated to 6 ml, and after 6 weeks, the mini-expander was removed and replaced by a textured, gel-filled (4 ml) mini-implant. The mini-implant had a surface texture that featured open, interconnecting pores. The mini-implant was placed inside the capsule created by the tissue expander. After 8 weeks, the mini-implant and the surrounding tissue were removed, processed and stained with hematoxylin and eosin to identify gross tissue morphology. FIG. 1B is a 5× image of remodeled capsule tissue 18 formed about the mini-implant 20 taken from the rat. The original capsule is no longer visible; what can be seen is the extensive tissue interaction with the open, interconnected pore texture of the implant 20.

It can be seen from FIG. 1B that the resulting tissue ingrowth pattern reflects the textured surface of the implant and shows significant tissue/material interaction. The tissue itself is composed of disorganized collagen fibers and contains numerous cell bodies.

This "remodeled" capsular tissue is less likely to contract over time.

EXAMPLE 2

Capsule Remodeling in an Breast Reconstruction Patient to Treat Capsular Contracture A 51 year old woman presents with encapsulated breasts arising from bilateral mastectomy and implant reconstruction. The implants are smooth surface saline implants. While initially the reconstructions were "good," over the years the breasts became harder, painful, and changed shape.

The physician removes the smooth surface implants from the breasts, leaving the capsular tissue largely intact. The physician implants new textured silicone implants into the pocket formed by the capsular tissue.

Although substantially the entire capsule of collagen-based, organized tissue fibers is left in the breasts, the capsular tissue, over time, is remodeled and reorganized by the interaction with the surfaces of the textured implants. Three years later, the breasts of the woman are soft and appear natural; the capsular tissue has not hardened and contracted even eight years later.

EXAMPLE 3

Breast Reconstruction in a Mastectomy Patient to Reduce Potential for Contracture At age 26, the patient was diagnosed with Ductal Carcinoma in Situ. Having seen other family members battling cancer, the patient made the decision to undergo a bilateral mastectomy. At the time of the mastectomy procedure, the patient chose not to have immediate reconstructive surgery.

Four years later, the patient decides to have implants placed. Because the skin of the patient's chest is taught and thin, the physician decides to gradually form a breast cavity for receiving a permanent prosthesis, using a tissue expander. The physician implants an uninflated tissue expander, having a textured surface with an average pore size of about 400 μm. Over a period of ten weeks, the physician periodically introduces fluid into the expanders to reach a final volume of 500 cc per expander. At this time, capsular tissue has formed around the expanders.

The physician removes the expanders, leaving as much of the capsular tissue intact as possible. The physician then implants permanent prostheses into the pockets formed by the capsular tissue. The permanent prostheses are saline implants having surface texture defined by an average pore size of about 700 μm.

The capsular tissue becomes disrupted and disorganized as it remodels and integrates into the new prosthesis that stimulate tissue integration with reduced capsule formation. Five years later, the breasts remain soft and natural in appearance as a result of the remodeling of the preformed capsule in response to the new texture.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments of this invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

In closing, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

What is claimed is:

1. A method for reconstructing a breast in a patient, the method comprising the steps of:
    introducing a first prosthesis having a first surface texture having no significant pores, into a breast;
    allowing the first prosthesis to remain in the breast for a time sufficient for an organized tissue capsule to form about the first prosthesis;
    removing the first prosthesis from the breast to form a breast cavity while leaving the organized capsular tissue intact in the breast; and
    introducing a second prosthesis into the breast cavity, the second prosthesis having a second surface texture having interconnected pores and an average pore size of greater than 600 μm in order to cause remodeling and/or disruption of said organized capsular tissue.

2. The method of claim 1 wherein the first prosthesis is an inflatable tissue expander.

3. The method of claim 1 further comprising the step of inflating the second prosthesis after the step of introducing the second prosthesis.

4. The method of claim 1 wherein the second texture surface is a non-bioresorbable surface.

5. A method for reconstructing a breast in a patient, the method comprising the steps of:

introducing a first prosthesis having a first surface texture having no significant pores, into a breast;

allowing the first prosthesis to remain in the breast for a time sufficient for an organized tissue capsule to form about the first prosthesis;

removing the first prosthesis from the breast to form a breast cavity while leaving the organized capsular tissue intact in the breast; and introducing a second prosthesis into the breast cavity, the second prosthesis having a second surface texture having interconnected pores and an average pore size of greater than 600 μm, in order to cause remodeling and/or disruption of said organized capsular tissue;

wherein the second surface texture is a porous, elastomeric silicone surface.

6. A method for reconstructing a breast in a patient, the method comprising the steps of:

introducing a first prosthesis having a smooth surface into a breast;

allowing the first prosthesis to remain in the breast for a time sufficient for an organized tissue capsule to form about the first prosthesis;

removing the first prosthesis from the breast to form a breast cavity while leaving the organized capsular tissue intact in the breast; and introducing a second prosthesis into the breast cavity, the second prosthesis having a second surface texture having interconnected pores and an average pore size of greater than 600 μm in order to cause remodeling and/or disruption of said organized capsular tissue.

* * * * *

UNITED STATES PATENT AND TRADEMARK OFFICE
CERTIFICATE OF CORRECTION

PATENT NO. : 8,801,782 B2
APPLICATION NO. : 13/327473
DATED : August 12, 2014
INVENTOR(S) : Barbara Nofrey et al.

It is certified that error appears in the above-identified patent and that said Letters Patent is hereby corrected as shown below:

Title Page Item (56)

On the Page 3, in column 2, under "Other Publications", line 15, delete "Fabriction," and insert -- Fabrication, --, therefor.

On the Page 3, in column 2, under "Other Publications", line 34, delete "Hydrosels," and insert -- Hydrogels, --, therefor.

On the Page 4, in column 2, under "Other Publications", line 57, delete "anistropy" and insert -- anisotropy --, therefor.

In the Specification

In column 1, line 33, delete "subgladular" and insert -- subglandular --, therefor.
In column 1, line 66, delete "reoccurance" and insert -- recurrence --, therefor.
In column 4, line 50, delete "a an" and insert -- an --, therefor.
In column 5, line 58, delete "by by" and insert -- by --, therefor.

Signed and Sealed this
Third Day of March, 2015

Michelle K. Lee
*Deputy Director of the United States Patent and Trademark Office*